United States Patent [19]

Tokita et al.

[11] Patent Number: 4,904,366

[45] Date of Patent: Feb. 27, 1990

[54] INSTRUMENT FOR DETERMINATION OF THE BASE SEQUENCE OF NUCLEIC ACID

[75] Inventors: Jiro Tokita, Kokubunji; Keiichi Nagai, Higashiyamato; Tamotu Simada, Akishima; Ken'ichi Watanabe, Kudamatsu; Ryusei Nakano, Kokubunji; Tomoaki Sumitani, Hachioji, all of Japan

[73] Assignee: Hitachi, Ltd., Tokyo, Japan

[21] Appl. No.: 128,885

[22] Filed: Dec. 4, 1987

[30] Foreign Application Priority Data

Dec. 12, 1986 [JP] Japan ................................. 61-294780

[51] Int. Cl.$^4$ ................................................. C25B 7/00
[52] U.S. Cl. ............................... 204/299 R; 204/182.8
[58] Field of Search ........................ 204/299 R, 182.8

[56] References Cited

U.S. PATENT DOCUMENTS 4,707,235 11/1987 Englert .............................. 204/182.8

OTHER PUBLICATIONS

Biggin et al., "Buffer Gradient Gels and $^{35}$S Label as an Aid to Rapid DNA Sequence Determination", *Proc. Nat. Acad. Sci. USA*, vol. 80, pp. 3963-3965, (1983).

Olsson et al., "Uniformly Spaced Banding Pattern in DNA Sequencing Gels by Use of Field—Strength Gradient", *Journal of Biochemistry and Biophysical Methods*, vol. 10, p. 84, (1984).

Primary Examiner—John F. Niebling
Assistant Examiner—Isabelle Rodriguez
Attorney, Agent, or Firm—Antonelli, Terry & Wands

[57] ABSTRACT

In the instrument for determination of the base sequence of the present invention, the ionic strength of a buffer solution in a gel is made lower at a detection part than in a region from the detection part towards a negative electrode. Therefore, at the detection part, the electric field intensity can be increased, resulting in a higher migration speed, and hence the electrophoretic pattern can be extended, so that the distance between two adjacent electrophoretic bands can be elongated.

Consequently, according to the present invention, the slit width can be narrowed relatively to the electrophoretic pattern without actually narrowing the slit width, and the resolving power can be enhanced without lowering the detection sensitivity.

9 Claims, 6 Drawing Sheets

INSTRUMENT FOR DETERMINATION OF THE BASE SEQUENCE OF NUCLEIC ACID

BACKGROUND OF THE INVENTION

This invention relates to an instrument for determination of the base sequence of nucleic acid, particularly to an instrument for determination of the base sequence of nucleic acid which can increase the number of base sequences to be determined by one run of electrophoresis by detecting nucleic acid fragments with a higher resolving power without impairing the detection sensitivity and thereby detecting longer nucleic acid fragments, as separated from each other.

Heretofore, the base sequence of nucleic acid has been determined according to Maxam-Gilbert method or dideoxy method of preparing nucleic acid fragments of various lengths labeled with a radioisotope, subjecting the fragments to separation by gel electrophoresis according to molecular weight, then visualizing the electrophoretic pattern by autoradiography, and reading the visualized pattern, as disclosed in Saibo Kogaku Vol. 1 (1982), pages 79–87 and 192–202. As a polymer matrix for the gel electrophoresis, there has heretofore been used a polyacrylamide gel in a plate form in which the concentration of buffer is uniform. Such features of the polyacrylamide gel are shown in FIGS. 1a, 1b and 1c.

However, there is recently known a gel in which the concentration of buffer is not uniform but has such a gradient that the concentration of buffer increases, as the buffer is nearer to the end of the migration lane, namely, to the anode, whereby an electrophoretic pattern is reduced at the region nearer the end of the migration lane to separate nucleic acid fragments in a broader range of molecular weight, as disclosed in Proc. Natl. Acad. Sci., U.S.A., Vol. 80, (1983), pp. 3963–3965. Such features of this gel are shown in FIGS. 1d, 1e and 1f.

The above two types of electrophoretic gels have heretofore been used only in a method comprising reading an electrophoretic pattern on the entire gel surface by autoradiography after the completion of electrophoresis (autoradiography method), and no consideration is given to their employment in a method comprising providing a detection part in the migration lane of an electrophoretic apparatus, detecting nucleic acid fragments successively arriving at the detection part by migration, and reading the electrophoretic pattern in real time [real-time direct detection method, see FIGS. 2a, 2b and 2c]. Said electrophoretic gels involve the following problems.

Generally, when nucleic acid fragments to be detected by gel electrophoresis are longer, the distance between the adjacent electrophoretic bands having a difference in length only by the length by which one base will be narrowed. On the other hand, counts of $\beta$-ray must be collected to more than a given degree in order to detect the nucleic acid fragments, and hence the slit width cannot be narrowed excessively to reduce the solid angle for effectively detecting the $\beta$-ray and lower the detection sensitivity. Employment of the conventional gel having a uniform concentration of buffer shown in FIGS. 1a, 1b and 1c has been disadvantageous in that if the nucleic acid fragments are longer, two or more electrophoretic bands will enter the gel in front of the slit at the same time, so that the individual electrophoretic bands cannot be detected as separated from each other [see FIGS. 3a, 3b and 3c]. The gel having a high concentration of buffer towards the tail end of migration lane, that is, towards the positive electrode shown in FIGS. 1d, 1e and 1f is advantageous in that many base sequences can be determined in the one and same gel when the autoradiography method is employed, but it has been disadvantageous in that when the real-time direct detection method is employed, the distance between the adjacent electrophoretic bands will be rather narrowed, so that it will be more difficult to detect longer nucleic acid fragments, as separated from each other.

SUMMARY OF THE INVENTION

An object of the present invention is to provide an instrument for determination of the base sequence of nucleic acid by real-time direct detection, which can increase the number of base sequences to be determined by one run of electrophoresis by detecting nucleic acid fragments with a higher resolving power without impairing the detection sensitivity, and thereby detecting longer nucleic acid fragments, as separated from each other.

The object described above can be achieved by extending an electrophoretic pattern at a detection part, and thereby elongating the distance between two adjacent electrophoretic bands. The electrophoretic pattern can be extended at the detection part by making the electric field intensity of an electrophoretic polymer matrix higher at the detection part than at least at one position in the region from the detection part towards the negative electrode.

Therefore, in this invention, the electric field intensity at the detection part is increased by lowering the ionic strength of buffer in the electrophoretic polymer matrix at the detection part, whereby the electrophoretic pattern is extended.

The low ionic strength described above can be achieved by lowering the concentration of buffer in the electrophoretic polymer matrix at the detection part.

A first feature of the invention consists in an instrument for determination of the base sequence of nucleic acid which comprises a detection part provided in a migration lane of an electrophoretic apparatus, nucleic acid fragments successively arriving at the detection part by migration being detected in real time, the ionic strength of a buffer in an electrophoretic polymer matrix being made higher at least at one position in a region from the detection part towards a negative electrode of the electrophoretic apparatus than at the detection part.

A second feature of the invention consists in an instrument for determination of the base sequence of nucleic acid which comprises a detection part provided in a migration lane of an electrophoretic apparatus, nucleic acid fragments successively arriving at the detection part by migration being detected in real time, and a step on means for controlling the migration speed of the nucleic acid fragments provided in the migration lane.

The ionic strength of buffer in the electrophoretic polymer matrix can be made higher at least at one position in a region from the detection part towards the negative electrode of the electrophoretic apparatus than at the detection part by making the concentration of buffer in the electrophoretic polymer matrix higher at least at one position in a region from the detection part towards the negative electrode of the electrophoretic apparatus than at the detection part.

The electrical resistance of an electrophoretic gel is inversely proportional to the ionic strength of a buffer in the gel. Since an electric current of equal level passes throughout the one and same gel, the electric field intensity in the gel is proportional to the electrical resistance, and furthermore the migration speed is proportional to the electric field intensity. Therefore, the lower the ionic strength of buffer in the gel, the higher the electrical resistance, the electric field intensity and the migration speed. Accordingly, by changing the ionic strength of the buffer at a desired part in the one and same gel, the migration speed can be controlled and hence the electrophoretic pattern can be extended or contracted at a desired part in the gel.

In the present invention, the ionic strength of buffer in the gel is made lower at the detection part than at least at one position in the region from the detection part towards the negative electrode. Therefore, at the detection part, the electric field intensity can be increased, resulting in a higher migration speed, and hence the electrophoretic pattern can be extended, so that the distance between two adjacent electrophoretic bands can be elongated.

By virtue of the structure described above, the slit width can be narrowed relatively to the electrophoretic pattern without actually narrowing the slit width, and the resolving power can be enhanced without lowering the detection sensitivity.

DETAILED DESCRIPTION OF THE PREFERRED EMBODIMENT

Figure 1A:
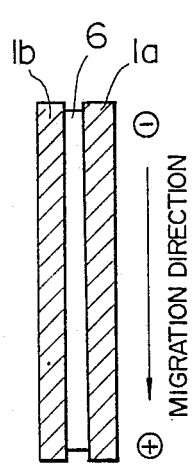
FIGS. 1a and 1d are vertical cross-sectional views of conventional electrophoretic gels.
Figure 1B:
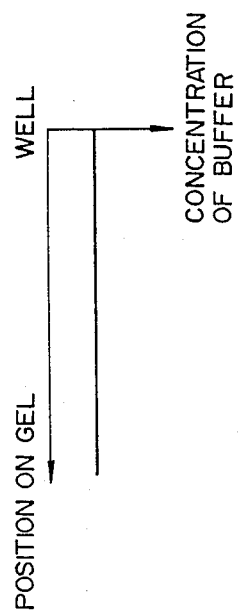
FIGS. 1b and 1e are graphs showing the buffer concentration distribution of buffer in these gels and correspond to FIGS. 1a and 1d respectively.
Figure 1C:
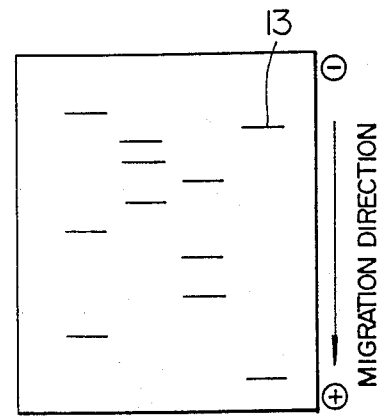
FIGS. 1c and 1f show electrophoretic patterns on these gels and correspond to FIGS. 1a and 1d respectively.
Figure 1D:
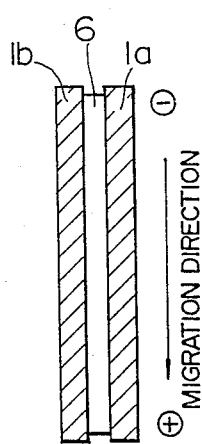
Figure 1E:
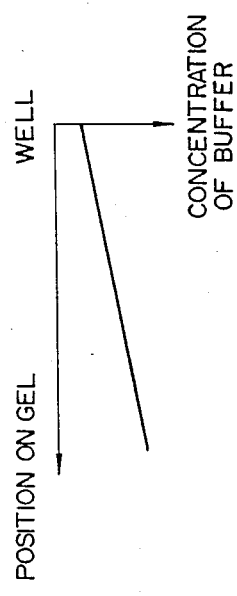
Figure 1F:
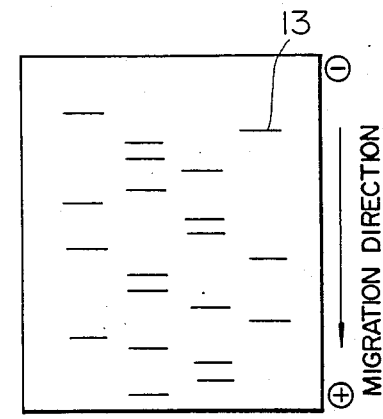
Figure 2A:
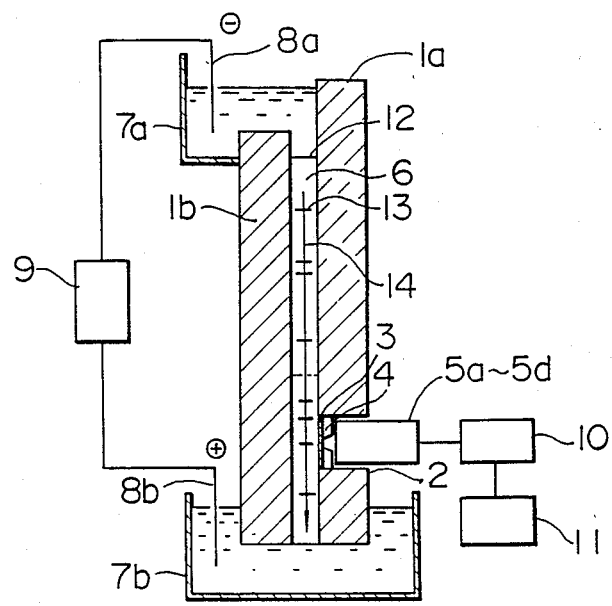
FIGS. 2a, 2b and 2c are a vertical cross-sectional view of an instrument according to one embodiment of the present invention, a front view thereof, and a graph showing the ionic strength distribution of a buffer in a gel used in the embodiment, respectively.
Figure 2B:
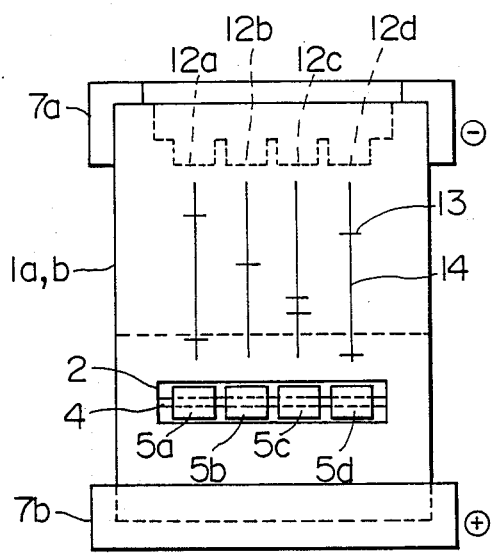
Figure 2C:
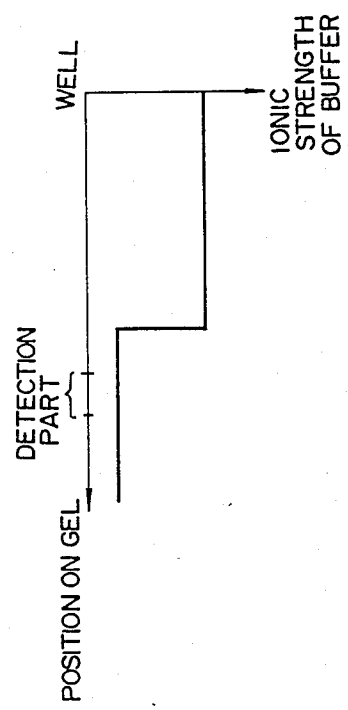

One embodiment of the present invention is explained below with reference to the drawings. FIGS. 2a, 2b and 2c show a vertical cross-sectional view of an instrument according to the embodiment, a front view thereof, and the ionic strength distribution of buffer solution used in the embodiment, respectively. In FIGS. 2a and 2b, on one or both of two electrophoretic plates 1a and 1b (provision on one of the plates being shown in FIGS. 2a and 2b) are provided a window 2 for detecting nucleic acid fragments, a partition wall 3 and a slit 4, and further radiation detectors 5a to 5d corresponding to four kinds of nucleic acid bases are mounted in the window 2. Between the two electrophoretic plates 1a and 1b is filled an electrophoretic gel 6 comprising a polyacrylamide gel which is an electrophoretic polymer matrix, and as shown in FIG. 2c, the ionic strength of a buffer in the gel is made lower at the detection part than at least at one position in the region from the detection part towards a negative electrode. The ionic strength of buffer solution can be thus partly lowered either by using a plurality of buffers and using a buffer solution having a low ionic strength among then at the detection part, or by using a single buffer and lowering its concentration at the detection part. At the upper ends and lower ends of the electrophoretic plates 1a and 1b are provided buffer tanks 7a and 7b, respectively, and a negative electrode 8a and a positive electrode 8b, respectively, and a direct current, high voltage power source 9 is connected to the two electrodes. Thus, a vertical type electrophoretic instrument is constructed. The outputs from the radiation detectors 5a to 5d are input into a signal processing unit 10 and, after processing, are output therefrom by an output unit 11.

Next, the working principle of this embodiment will be described below. First, mixtures of nucleic acid fragments having various lengths labeled with radioisotope $^{32}P$ and prepared according to the Maxam-Gilbert method or the dideoxy method and are poured into wells 12a to 12d which are provided at the upper end of the gel, each according to four kinds of nucleic acid base. Subsequently, a direct current voltage (about 50 V/cm) is applied to the negative electrode 8a and the positive electrode 8b from the direct current, high voltage power source 9, whereby the nucleic acid fragments migrate by electrophoresis and are separated from one another according to their molecular weight, and nucleic acid fragments having an equal length form one electrophoretic band 13. The shorter the nucleic acid fragments, the higher the migration speed. Therefore, the electrophoretic band of the shorter nucleic fragments reach the front of the radiation detectors 5a to 5b faster, and the $\beta$-ray radiated from the label $^{32}P$ is detected by the detectors. The adjacent electrophoretic bands are detected as separated from each other by way of the slit 4. The signals output from the detectors is led to the signal processing unit 10 and processed. A nucleic acid base corresponding to its detected signal is automatically identified among the four kinds of bases, whereby an electrophoretic pattern can be read. Thus, in the instrument of this embodiment, an electrophoretic pattern can be directly read in real time during the electrophoresis without using a photographic film or the like and the base sequence can be determined thereby.

Figure 3A:
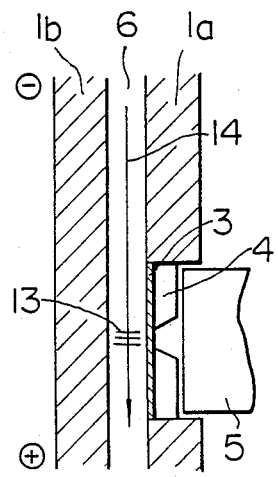
FIGS. 3a, 3b and 3c are a vertical cross-sectional view of a conventional gel in which the ionic strength of a buffer is uniform, a graph showing the ionic strength distribution of buffer in the gel, and a diagram showing one example of output from a detector in the case of using this gel, respectively.
Figure 3B:
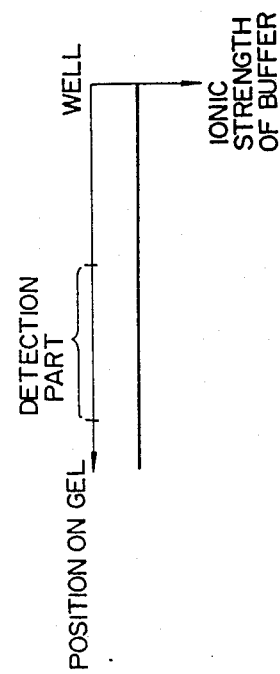
Figure 3C:
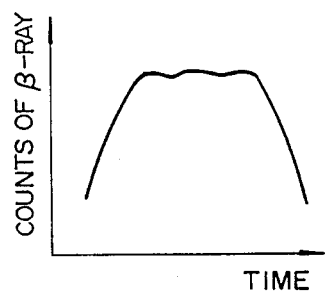

As described above, the longer the nucleic acid fragments to be detected, the narrower the distance between the adjacent electrophoretic bands. The electrophoretic bands formed by nucleic acid fragments having a difference in length only by the length of one base. On the other hand, it is necessary to collect the counts of $\beta$-ray to more than a given degree in order to detect the nucleic acid fragments, and hence the slit width cannot be narrowed excessively to reduce the solid angle for effectively detecting the β-ray. Therefore, employment of a conventional gel in which both concentration and ionic strength of a buffer are uniform has been disadvantageous. This is because if the length of nucleic acid fragments to be detected is as long as 100 to 150 bases, two or more electrophoretic bands will enter the gel in front of the slit at the same time, and the individual electrophoretic bands will not be detected in their separated form (see FIGS. 3a, 3b and 3c).

Figure 4A:
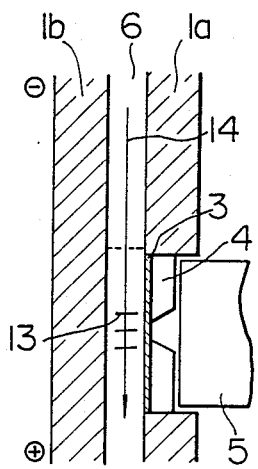
FIG. 4a, 4b and 4c are a vertical cross-sectional view of the gel used in the above embodiment, a graph showing the ionic strength distribution of buffer in the gel, and a diagram showing one example of output from a detector in the above embodiment, respectively.
Figure 4B:
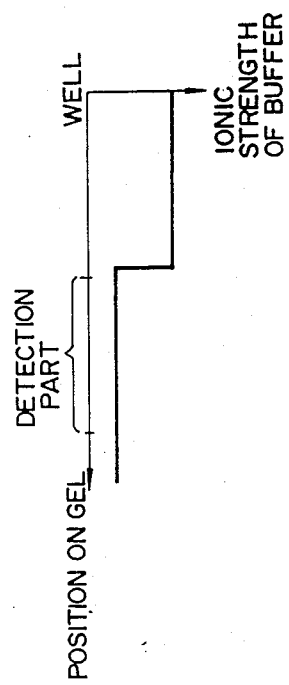
Figure 4C:
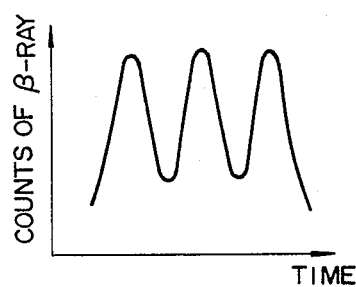
Figure 5A:
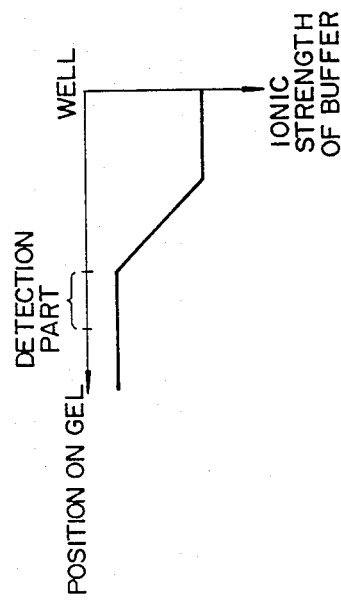
FIGS. 5a, 5b, 5c and 5d are graphs showing the ionic strength distributions of buffers in gels of modifications of the above embodiment.
Figure 5B:
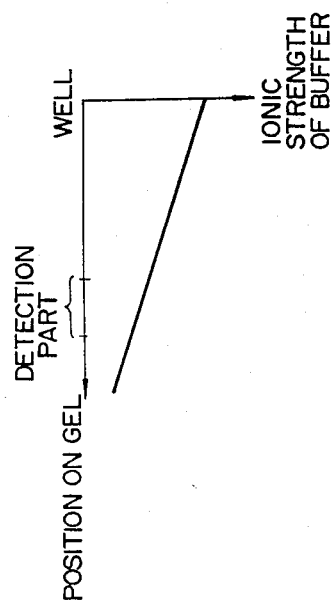
Figure 5C:
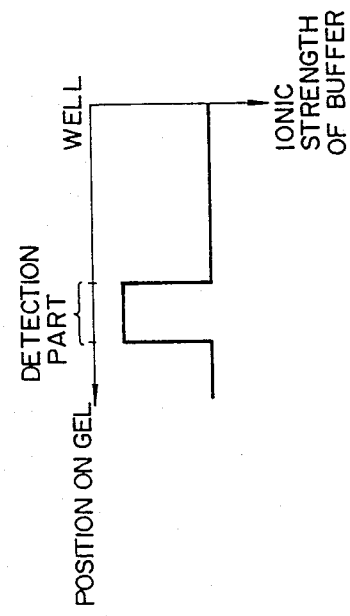
Figure 5D:
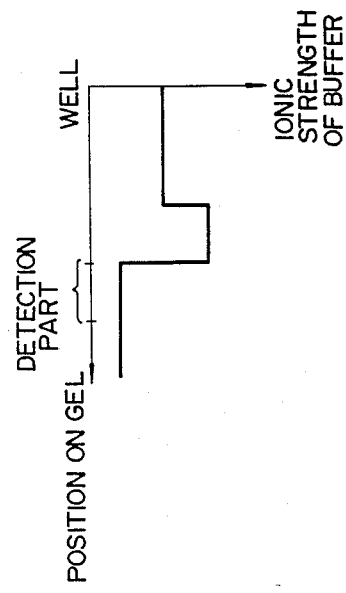

Accordingly, in the present embodiment, the concentration of trihydroxyaminomethane-boric acid-ethylenediaminetetracetic acid (TBE) buffer in the gel is adjusted to twice the conventional concentration in the region from the detection part towards the negative electrode and to one-half of the conventional concentration at the detection part and in the region from the detection part towards the positive electrode, whereby the ionic strength of the buffer is made lower at the detection part than in the region from the detection part towards the negative electrode. As a result, the electrical resistance of the gel is increased at the detection part, and hence the electric field intensity is also increased under a constant electric current, so that the migration speed is increased, resulting in extension of the electrophoretic pattern. Therefore, the slit width can be narrowed relatively to the electrophoretic pattern without actually narrowing the slit width, and hence the resolving power can be increased without impairing the detection sensitivity (see FIGS. 4a, 4b, and 4c.

Similar effects can be obtained with other distribution of the ionic strength of buffer than that shown in FIG. 2c, for example, with those shown in FIGS. 5a to 5d. In particular, the ionic strength distribution in the region from the detection part towards the positive electrode has no direct influence on the effects described above.

Figure 6A:
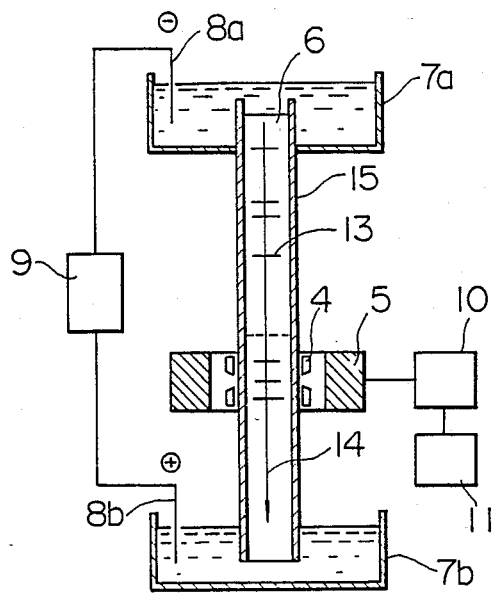
FIGS. 6a, 6b and 6c are a vertical cross-sectional view of an instrument according to another embodiment of the present invention, a front view thereof, and a graph showing the ionic strength distribution of a buffer in a gel used in this embodiment, respectively.
Figure 6B:
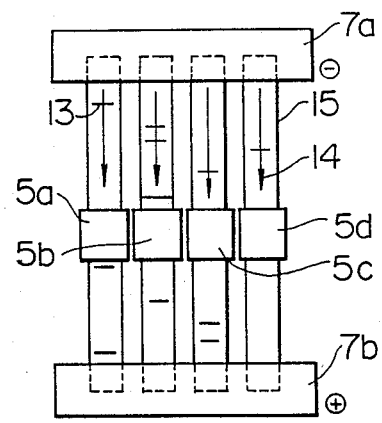
Figure 6C:
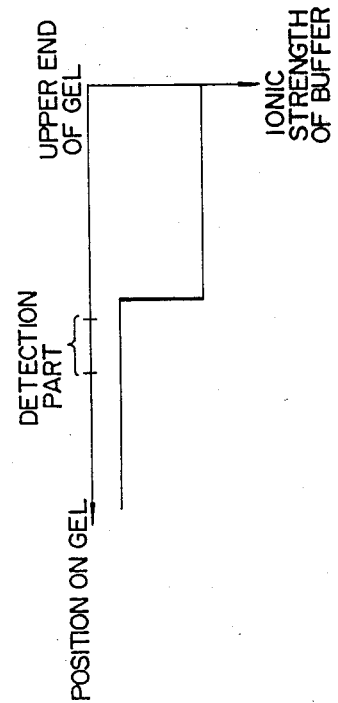

Next, another embodiment of the present invention will be described below. FIGS. 6a, 6b and 6c show a vertical cross-sectional view of an instrument according to this embodiment, a front view thereof, and the ionic strength distribution of a buffer used in this embodiment, respectively. In FIGS. 6a and 6b, glass tubes 15 are provided for four kinds of nucleic acid bases, respectively, and ring-shaped slits 4 and radiation detectors 5a to 5d are provided around the glass tubes 15, respectively, at the detection part. Each of the glass tube 15 is packed with a polyacrylamide gel serving as an electrophoretic gel 6, and the concentration of TBE buffer in the gel is adjusted to twice the conventional concentration in the region from the detection part towards the negative electrode and to one-half of the conventional concentration at the detection part and in the region from the detection part towards the positive electrode. Therefore, as shown in FIG. 6c, the ionic strength of the buffer is lower at the detection part than in the region from the detection part towards the negative electrode. At the upper ends and the lower ends of glass tubes 15 are provided buffer tanks 7a and 7b, respectively, and a negative electrode 8a and a positive electrode 8b, respectively, and a direct current, high voltage power source 9 is connected to the two electrodes. The outputs from the radiation detectors 5a to 5d are input into a signal processing circuit 10 and, after processing, are output by an output unit 11.

The working principle of the present embodiment is substantially the same as that of the preceding embodiment. However, in the present embodiment, mixtures of nucleic acid fragments having different lengths are applied not to the wells but to the upper ends of the gels in the glass tubes, and β-ray detection is carried out at the entire circumferences of columnar gels. Therefore, the solid angle for detecting the β-ray in the present embodiment is larger than in the preceding embodiment in with the β-ray is detected at one side or both sides of plate-formed gel, and the β-ray counts obtained in the present embodiment is more than twice or more than that obtained by the one-side or the both-side detection, respectively, in the preceding embodiment. Therefore, according to the present embodiment, the resolving power can be enhanced without impairing the detection sensitivity as in the preceding embodiment, and moreover the detection sensitivity can be elevated.

According to the present invention, the electrophoretic pattern can be extended at the detection part, and hence the slit width can be narrowed relatively to the electrophoretic pattern without actually narrowing the slit width, so that the resolving power can be enhanced without lowering the detection sensitivity.

Therefore, even if nucleic acid fragments to be detected are so long that the distance between the adjacent electrophoretic bands is narrowed, the two electrophoretic bands can be detected as separated from each other, and hence the number of base sequences to be determined by one run of electrophoresis can be increased.

What is claimed is:

1. An apparatus for determination of a base sequence of a nucleic acid, comprising:
    an electrophoretic matrix having a migration lane and buffer therein;
    means for introducing sample containing nucleic acid fragments into a first end of said electrophoretic matrix;
    means for applying an electrical potential between positive and negative electrodes for electrophoresis so that a negative potential is applied to said first end of said electrophoretic matrix and a positive potential is applied to a second end of said electrophoresis matrix;
    detection means located at said migration lane and substantially separated from said first end of said electrophoretic matrix for detecting in real time the nucleic acid fragments successively arriving at a detection part; and
    the ionic strength of said buffer in said electrophoretic matrix is higher at least at one position in a region spaced from the detection part towards said first end than at the detection part.

2. An apparatus for determination of the base sequence of nucleic acid according to claim 1, wherein the concentration of buffer in the electrophoretic matrix is higher at least at said first end position in the region from the detection part towards the negative electrode of the electrophoretic apparatus than at the detection part.

3. An apparatus according to claim 1, wherein the electrophoretic matrix has a plurality of migration lanes and the detection means are provided such that the nucleic acid fragments on each migration lane can be separately detected.

4. An apparatus according to claim 1, wherein the nucleic acid fragments are labeled with a radioisotope.

5. An apparatus according to claim 1, wherein the detection means are for detecting a radiation.

6. An apparatus according to claim 1, wherein the concentration of the buffer at the detection part is about one-fourth of that at the region from the detection part towards the first end of the electrophoretic matrix.

7. An apparatus according to claim 1, wherein the electrophoretic matrix is surrounded by the detection means.

8. A method for elongating a migration pattern of nucleic acid fragments when determining a base sequence of nucleic acid comprising:

providing a electrophoretic matrix having a migration lane from a first end of a second end and a buffer therein, the ionic strength of said buffer being higher at least at one position in a region between said first end and a detection part separated by a substantial distance from the first end that at said detection part;

introducing sample containing nucleic acid fragments into said first end of said electrophoretic matrix;

applying voltage between a positive and a negative electrode for electrophoresis with a negative potential applied to said first end of the electrophoretic matrix and a positive potential applied to said second end of said electrophoretic matrix; and detecting in real time the nucleic fragments successively arriving at said detection part.

9. The method according to claim 8 wherein the ionic strength is controlled by making the concentration of the buffer in the electrophoretic matrix higher at least in said first position in the region from the detection part towards the negative electrode than at the detection part.

* * * * *